United States Patent [19]

Camaggi et al.

[11] Patent Number: 5,716,974
[45] Date of Patent: Feb. 10, 1998

[54] HETEROBICYCLIC COMPOUNDS WITH FUNGICIDAL ACTIVITY

[75] Inventors: Giovanni Camaggi, Novara; Lucio Filippini, San Donato Milanese; Marilena Gusmeroli, Monza; Silvia Mormile, Turin; Isabella Venturini, Milan; Carlo Garavaglia, Cuggiono; Ernesto Signorini, Malnate, all of Italy

[73] Assignee: Isagro S.p.A., Milan, Italy

[21] Appl. No.: 779,041

[22] Filed: Jan. 6, 1997

Related U.S. Application Data

[62] Division of Ser. No. 368,641, Jan. 4, 1995, abandoned.

[30] Foreign Application Priority Data

Jan. 11, 1994 [IT] Italy ................. MI94A0018

[51] Int. Cl.⁶ ................. C07D 513/04; A01N 43/90
[52] U.S. Cl. ................. 514/368; 548/126; 548/154
[58] Field of Search ................. 514/368; 548/154

[56] References Cited

U.S. PATENT DOCUMENTS 5,366,984  11/1994  Schuetz .................. 514/361
5,384,325  1/1995  Camaggi .................. 514/365

FOREIGN PATENT DOCUMENTS 508901    10/1992  European Pat. Off. ........ 548/204
0 554 957  8/1993  European Pat. Off. .
0 625 520  11/1994  European Pat. Off. .

*Primary Examiner*—Robert Gerstl
*Attorney, Agent, or Firm*—Oblon, Spivak, McClelland, Maier & Neustadt, P.C.

[57] ABSTRACT

Compounds based on heterobicyclic derivatives, of general formula (I):

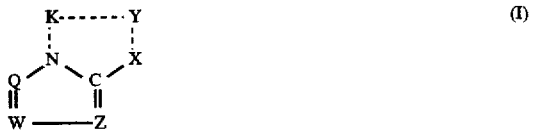

possessing fungicidal activity.

13 Claims, No Drawings

HETEROBICYCLIC COMPOUNDS WITH FUNGICIDAL ACTIVITY

This application is a Division of application Ser. No. 08/368,641, filed on Jan. 4, 1995, now abandoned.

This invention relates to high antifungal activity compounds based on heterobicyclic derivatives.

More specifically, the invention relates to high antifungal activity compounds based on heterobicyclic derivatives, the process for their preparation and their use in the agricultural, human and veterinary field for controlling pathogenic fungi. Compounds based on pyrrole[2,1-b]- and imidazo[2,1-b]-thiazoles possessing fungicidal activity for use in the agricultural field are known from Italian patent application Mi 92 A 000225. However the fungicidal activity of these compounds is limited in time. The present applicant has now discovered compounds based on heterobicyclic derivatives possessing higher fungicidal activity than compounds described in the known art and able to provide better protection against attack by pathogenic fungi not only in the agricultural field but also in the human and veterinary field. Certain compounds also demonstrate interesting activity against acarids, nematoda and insects damaging to plants.

The present invention therefore provides compounds based on heterobicyclic derivatives, of general formula (I):

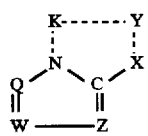
(I)

in which:

Y, Q, W and Z, which can be identical or different, represent one of the following groups:

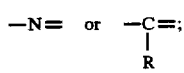

K represents an —N(R)— group or one of the groups which define Y, Q, W and Z;

X, when K is an —N(R)— group, represents one of the groups which define Y, Q, W and Z; when K is one of the groups which define Y, Q, W and Z, it represents a sulphur or oxygen atom, or one of the following groups: —N(R)—, —N=C(R)—, —C(R)=C(R)—, —C(R)=N—;

R represents one of the T, Ra or Ch groups defined hereinafter, such that at least one of said X, K, Y, Q, W and Z groups contains a T group;

T represents one of the following groups of general formula (II), (III), (IV) and (V):

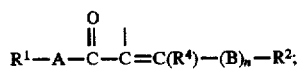
(II)

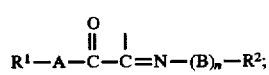
(III)

(IV)

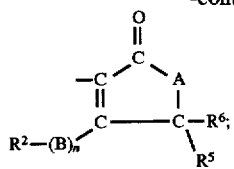
(V)

in which:

A and B, identical or different, represent an oxygen or sulphur atom or an —N($R^3$)— group;

$R^1$, $R^2$, $R^3$, $R^4$, $R^5$ and $R^6$, identical or different, represent a hydrogen atom or a $C_1$-$C_4$ linear or branched alkyl or haloalkyl group;

n can be 0 or 1;

Ra represents a hydrogen atom, a halogen atom such as fluorine, chlorine, bromine or iodine; a cyano group; a $C_1$-$C_4$ linear or branched alkyl or haloalkyl group; a $C_1$-$C_4$ linear or branched alkoxy or haloalkoxy group; a $C_1$-$C_4$ linear or branched alkoxyalkyl or haloalkoxyalkyl group; a $C_1$-$C_4$ linear or branched carboalkoxy group; a $C_3$-$C_8$ cycloalkyl or cycloalkoxyalkyl group; or, when Y and K are a —C(Ra) group, the two Ra groups can also jointly form a chain:

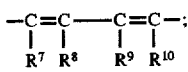

in which:

$R^7$, $R^8$, $R^9$ and $R^{10}$, identical or different, represent a hydrogen atom, a halogen atom such as fluorine, chlorine, bromine or iodine; a $C_1$-$C_4$ linear or branched alkyl or haloalkyl group; a $C_1$-$C_4$ linear or branched alkoxyalkyl or haloalkoxyalkyl group; a $C_3$-$C_8$ cycloalkyl or cycloalkoxyalkyl group; a $C_7$-$C_9$ arylalkyl or aryloxyalkyl group;

Ch represents a group of general formula (VI):

(VI)

in which:

D and F, identical or different, represent a direct bond; an oxygen, sulphur or nitrogen atom; a nitrogen atom substituted with a $C_1$-$C_3$ alkyl group; or a carbonyl group;

E represents a direct bond; a $C_6$,$C_{10}$ aryl group optionally substituted; a penta- or hexa-atomic heteroaryl group optionally benzocondensed and/or substituted;

m and p, identical or different, are a whole number between 0 and 4;

with the proviso that:

when in a compound of general formula (I) X represents a sulphur atom, Y represents a =C(Ra)— group or a =C(Ch)— group, assuming for Ra or Ch the meanings of hydrogen atom or $C_1$-$C_4$ linear or branched alkyl or haloalkyl group; K represents a =C(T)— group where T represents a group of general formula (II) in the particular case in which A and B represent an oxygen atom, n is 1 and $R^4$ represents a hydrogen atom; Z represents an =N— group or a =C(Ra)— group where Ra represents a hydrogen atom; W represents a =C(Ra)— group where Ra represents a hydrogen atom or a $C_1$-$C_6$ linear or branched alkyl or haloalkyl group, or W represents a =C(Ch)— group where Ch represents a hydrogen atom, or a $C_1$-$C_6$ linear or branched alkyl group or a phenyl group, said $C_1$-$C_6$ alkyl and phenyl groups being optionally substituted with: halogens such as fluorine, chlorine, bromine or iodine, a $C_1$–$C_4$ linear or branched alkyl group, a $C_1$–$C_4$ linear or branched alkoxy or haloalkoxy group, or a phenyl or phenoxy group;

when in a compound of general formula (I) X represents a sulphur atom, Y represents a =C(Ra)— group or a =C(Ch)— group, assuming for Ra or Ch the meanings of hydrogen atom or $C_1$–$C_4$ linear or branched alkyl or haloalkyl group; K represents a =C(T)— group where T represents a group of general formula (II) in the particular case in which n is 1 and B represents an oxygen atom, or T represents a group of general formula (III) in the particular case in which n is 1 and B represents an oxygen atom; Q represents an =N— group; Z represents an =N— group or a =C(Ra)— group where Ra represents a hydrogen atom or a $C_1$–$C_4$ linear or branched alkyl group; W represents a =C(Ra)— group or a =C(Ch)— group where Ra and Ch have the aforesaid meanings for the compounds of general formula (I).

The compounds of general formula (I) can present at least one E/Z isomerism. It is within the spirit of the present invention to consider both the isomerically pure compounds of general formula (i) and their mixtures.

The compounds of general formula (I) represent antifungals useful in the agricultural, human and veterinary fields. Many of these compounds can also exhibit insecticide or acaricide activity in the agricultural field and fully fall within the scope of the present patent.

In defining the compounds of general formula (I), the bonds between K, Y and X are shown dashed as they can be single or double depending on the meaning of K, Y and X.

Examples of T groups are: 1-methoxycarbonyl-2-methoxyethen-1-yl, 1-ethoxycarbonyl-2-methoxyethen-1-yl, 1-methoxycarbonyl-2-ethoxyethen-1-yl, 1-methoxycarbonyl-2-(1,1,2,2-tetrafluoroethoxy)ethen-1-yl, 1-methoxycarbonyl-2-thiomethoxyethen-1-yl, 1-methoxycarbonyl-2-ethylethen-1-yl, methoxycarbonyloxomethyl, methoxyiminomethoxycarbonylmethyl, ethoxyiminomethoxycarbonylmethyl, ethyliminomethoxycarbonylmethyl, 1-(N-methylcarbamoyl)-2-methoxyethen-1-yl, 1-(N-methylcarbamoyl)-2-thiomethoxyethen-1-yl, 4-methoxy-2(5H)furanon-3-yl, 3-methyl-4-methoxy-2(5H)furanon-3-yl, 3,3-dimethyl-4-methoxy-2(5H)furanon-3-yl, 4-methoxy-2(5H)-pyrrolidinon-3-yl, etc.

Examples of Ra groups are: methyl, ethyl, trifluoromethyl, trifluoroethyl, methoxy, ethoxy, 1,1,1-trifluoroethoxy, etc.

In the definitions of the compounds of general formula (I):

$C_6$,$C_{10}$ aryl group means the phenyl group and the naphthyl group;

penta- or hexa-atomic heterocyclic groups mean for example the following heteroaromatic rings: pyridyl, pyrimidyl, piridazyl, thienyl, furyl, pyrrolidyl, triazolyl, imidazolyl, isooxazolyl, oxazolyl, thiazolyl, etc.

aryl or heteroaryl groups optionally substituted means that said aryls or heteroaryls can be substituted with:

one or more groups, identical or different, chosen from the following: $C_1$–$C_6$ linear or branched alkyl or haloalkyl; $C_1$–$C_6$ linear or branched alkoxy or haloalkoxy; $C_2$–$C_8$ linear or branched alkoxyalkyl; $C_1$–$C_6$ linear or branched haloalkoxyalkyl; $C_2$–$C_8$ carboalkoxy group; $C_2$–$C_8$ carbamoyl; a cyano group; or a halogen atom such as fluorine, chlorine, bromine or iodine.

In the definition of the group of general formula (VI), the alkylene chains, defined as —($C_mH_{2m}$)— and —($C_pH_{2p}$)—, mean linear or branched.

Examples of Ch groups in accordance with the aforesaid definitions are:

methyl, isopropyl, t-butyl, cyclopropyl, cyclobutyl, cyclopentyl, cyclohexyl, cycloheptyl;

methoxymethyl, methoxyethyl, isopropoxymethyl, cyclopropyloxymethyl, cyclohexyloxymethyl;

trifluoromethyl, trichloromethyl, tetrafluoroethyl, perfluorobutyl;

tetrafluoroethoxymethyl, tetrafluorothioethoxymethyl;

phenoxymethyl, 2-chlorophenoxymethyl, 4-chlorophenoxymethyl, 2,4-dichlorophenoxymethyl;

2-methylphenoxyphenyl, 2-cyanophenoxyphenyl, 2-chloro-4-(2-cyanophenoxy)phenyl;

phenyl, 2-chlorophenyl, 4-chlorophenyl, 2,4-dichlorophenyl, 2,4-difluorophenyl, 2-methoxyphenyl, 4-methoxyphenyl, 4-isopropoxyphenyl, 4-cyclopropoxyphenyl, 4-cyclohexylmethoxyphenyl, 4-tetrafluoroethoxyphenyl, 4-trifluoromethylphenyl;

4-phenoxyphenyl, 3-phenoxyphenyl, 4-(3-trifluoromethylpyridyl-2-oxy)phenyl, 4-(4-trifluoromethylpyridyl-2-oxy)phenyl, 4-(4,6-dimethylpyrimidyl-2-oxy)phenyl, 4-(4-phenyl-5-trifluoromethylisothiazol-2-yloxy)phenyl;

6,4-dimethylpyrimidyl-2-yl, 2-trifluoromethyl-5-methylthiazol-4-yl, 5-(4-chlorophenyl)isooxazol-3-yl;

6-phenoxypyrimid-4-yloxy, 6-phenylpyrimid-4-yloxy, 5-(4-chlorophenyl)-4-methylthiazolyl-2-oxy, 5-trifluoromethylpyridyl-2-oxy, 5-trifluoromethyl-3-chloropyridyl-2-oxy, benzoxazol-2-yloxy, benzoisothiazol-2-yloxy;

5-t-butylisooxazol-3-yl, 5-(2-methylphenyl)isooxazol-3-yl, 5-(2-fluorophenyl)isooxazol-3-yl, 5-(2-chlorophenyl)-isooxazol-3-yl; etc.

In order to better illustrate the invention and without in any way being limitative thereof, Schedule 1 shows some examples of heterobicyclic structures falling within general formula (I).

SCHEDULE 1

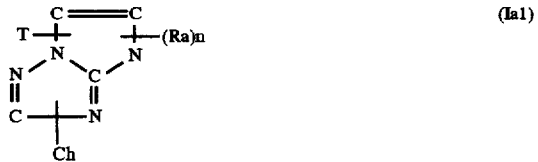

(Ia1)

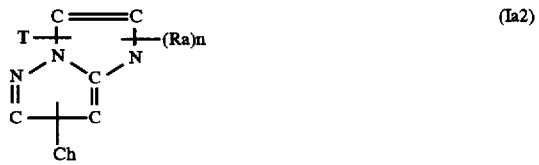

(Ia2)

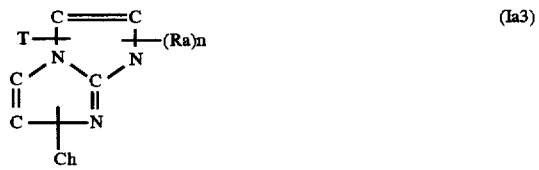

(Ia3)

-continued
SCHEDULE 1
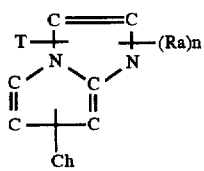 (Ia4)
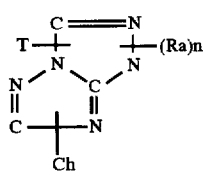 (Ib1)
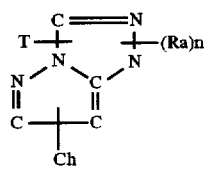 (Ib2)
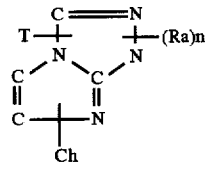 (Ib3)
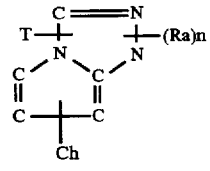 (Ib4)
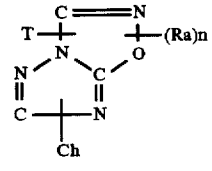 (Ic1)
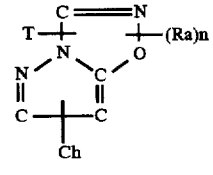 (Ic2)
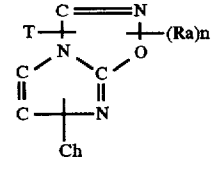 (Ic3)
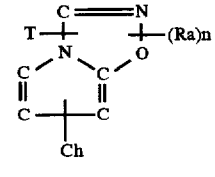 (Ic4)
-continued
SCHEDULE 1
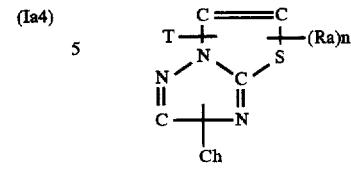 (Id1)
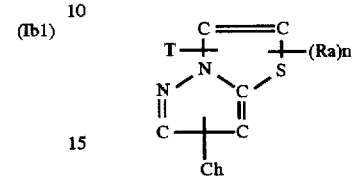 (Id2)
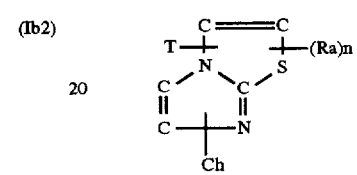 (Id3)
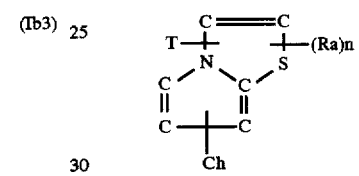 (Id4)
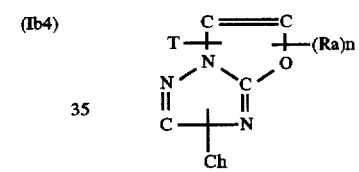 (Ie1)
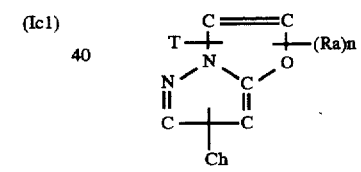 (Ie2)
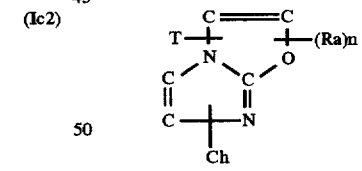 (Ie3)
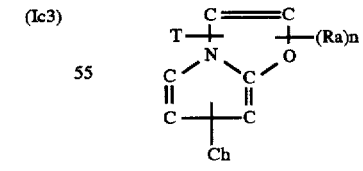 (Ie4)
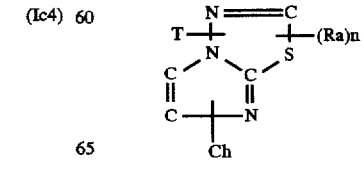 (If1)

-continued
SCHEDULE 1

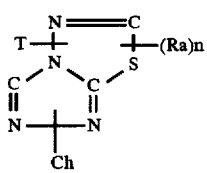 (If2)

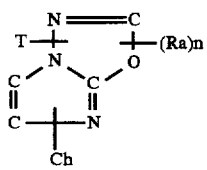 (Ig1)

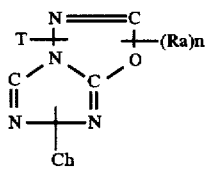 (Ig2)

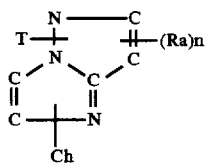 (Ih1)

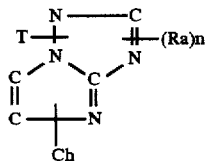 (Ih2)

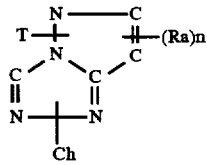 (Ih3)

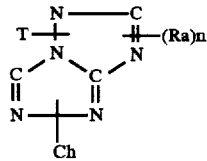 (Ih4)

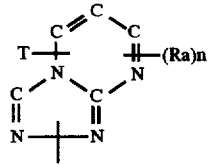 (Ii1)

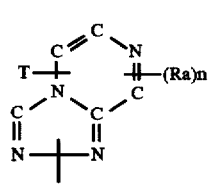 (Ii2)

In Schedule 1 above, the T, Ch and Ra groups have the aforesaid meanings, and in addition in the adopted graphical convention said groups are intended to be located in any position of the bicyclic system, wherever it is possible to form a covalent bond. For a better definition, Schedule 2 below shows some of the structures of general formula (I) given in Schedule 1.

SCHEDULE 2

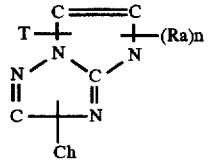 (Ia1)

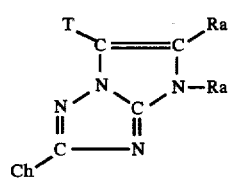 (Ia11)

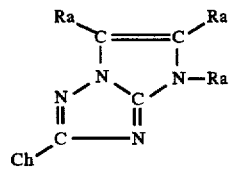 (Ia12)

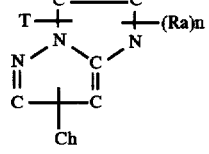 (Ia2)

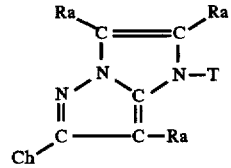 (Ia21)

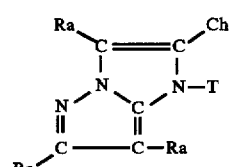 (Ia22)

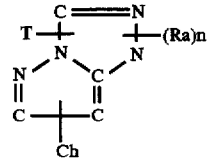 (Ib2)

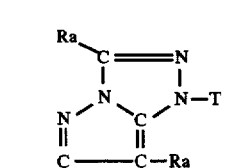 (Ib21)

-continued
SCHEDULE 2

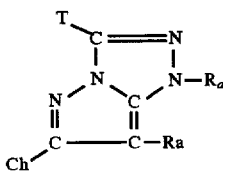 (Ib22)

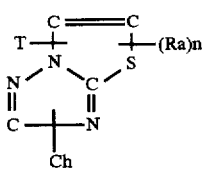 (Id1)

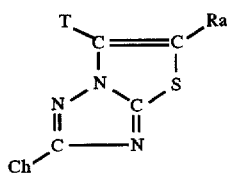 (Id11)

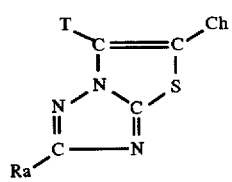 (Id12)

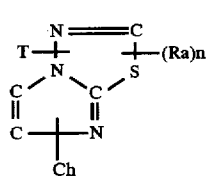 (If1)

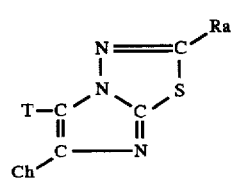 (If11)

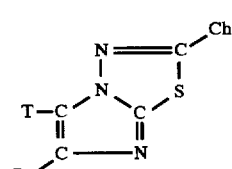 (If12)

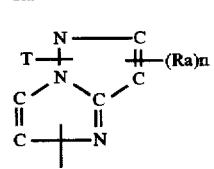 (Ih1)

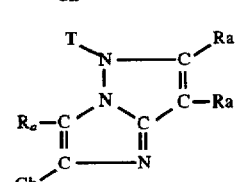 (Ih11)

-continued
SCHEDULE 2

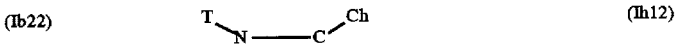 (Ih12)

Compounds of general formula (I) not illustrated in the examples, but equally interesting for their biological activity, comprise (using the numeration reported by Katrinsky A. in "Comprehensive Heterocyclic Chemistry" (1984), Vol. 6, pp 956–965, Pergamon Press Publ.):

2-methyl-5-(1-methoxycarbonyl-2-methoxyethen-1-yl)-6-(2-chlorophenyl)thiazolo[3,2-b][1,2,4]triazole;

2-methyl-5-(1-methoxycarbonyl-2-methoxyethen-1-yl)-6-(4-chlorophenyl)thiazolo[3,2-b][1,2,4]triazole;

2-methyl-5-(1-methoxycarbonyl-2-methoxyethen-1-yl)-6-(4-methoxyphenyl)thiazolo[3,2-b][1,2,4]triazole;

2-methyl-5-(1-methoxycarbonyl-2-methoxyethen-1-yl)-6-(2-chlorophenoxymethyl)thiazolo[3,2-b][1,2,4]triazole;

2-methyl-5-(1-methoxycarbonyl-2-methoxyethen-1-yl)-6-(4-chlorophenoxymethyl)thiazolo[3,2-b][1,2,4]triazole;

2-methyl-5-(1-methoxycarbonyl-2-methoxyethen-1-yl)-6-(2-cyanophenoxymethyl)thiazolo[3,2-b][1,2,4]triazole;

2-methyl-5-(1-methoxycarbonyl-2-methoxyethen-1-yl)-6-(4-cyanophenoxymethyl)thiazolo[3,2-b][1,2,4]triazole;

2-methyl-5-(1-methoxycarbonyl-2-methoxyethen-1-yl)-6-(2-methylphenoxymethyl)thiazolo[3,2-b][1,2,4]triazole;

2-methyl-5-(1-methoxycarbonyl-2-methoxyethen-1-yl)-6-(4-methoxyphenoxymethyl)thiazolo[3,2-b][1,2,4]triazole;

2-methyl-5-(methoxyiminomethoxycarbonylmethyl)-6-(2-chlorophenoxymethyl)thiazolo[3,2-b][1,2,4]triazole;

2-methyl-5-(methoxyiminoethoxycarbonylmethyl)-6-(4-methoxyphenoxymethyl)thiazolo[3,2-b][1,2,4]triazole;

3-(1-methoxycarbonyl-2-methoxyethen-1-yl)-6-(4-chlorophenyl)thiazolo[2,3-c][1,2,4]triazole;

2-(4-chlorophenyl)-5-(1-methoxycarbonyl-2-methoxyethen-1-yl)-6-methylimidazolo[2,1-b]-1,3,4-thiadiazole;

2-(4-methoxyphenyl)-5-(1-methoxycarbonyl-2-methoxyethen-1-yl)-6-methylimidazolo[2,1-b]-1,3,4-thiadiazole;

2-t-butyl-5-(1-methoxycarbonyl-2-methoxyethen-1-yl)-6-methylimidazolo[2,1-b]-1,3,4-thiadiazole;

2-(4-chlorophenyl)-5-(methoxyiminomethoxycarbonylmethyl)-6-methylimidazolo[2,1-b]-1,3,4-thiadiazole;

2-(4-methoxyphenyl)-5-(methoxyiminomethoxycarbonylmethyl)-6-methylimidazolo[2,1-b]-1,3,4-thiadiazole;

2-(4-phenoxyphenyl)-5-(methoxyiminomethoxycarbonylmethyl)-6-methylimidazolo[2,1-b]-1,3,4-thiadiazole;

2-[4-(3-trifluoromethylpyridyl-2-oxy)phenyl]-5-(methoxyiminomethoxycarbonylmethyl)-6-methylimidazolo[2,1-b]-1,3,4-thiadiazole;

2-t-butyl-5-(methoxyiminomethoxycarbonylmethyl)-6-methylimidazolo[2,1-b]-1,3,4-thiadiazole;

3-(1-methoxycarbonyl-2-methoxyethen-1-yl)-6-(4-chlorophenyl)-1,2,4-triazolo[3,4-b][1,2,4]thiadiazole;

3-(1-methoxycarbonyl-2-methoxyethen-1-yl)-6-(4-t-butyl)-1,2,4-triazolo[3,4-b][1,2,4]thiadiazole;

2-(4-chlorophenyl)-5-(1-methoxycarbonyl-2-methoxyethen-1-yl)-6-methyloxazolo[3,2-b][1,2,4]triazole;

1-(1-methoxycarbonyl-2-methoxyethen-1-yl)-3-methyl-6-phenyl-1H-pyrazolo[1,5-c]-1,2,4-triazole;

5-(1-methoxycarbonyl-2-methoxyethen-1-yl)-6-phenyl-5H-pyrazolo[1,5-c]-1,2,4-triazole;

1-methyl-3-(1-methoxycarbonyl-2-methoxyethen-1-yl)-6-(4-methoxyphenyl)-3H-[1,2,4]triazolo[3,2-c]-1,2,4-triazole;

3-phenyl-3-(1-methoxycarbonyl-2-methoxyethen-1-yl)-6-methyl-3H-imidazo[1,2-b][1,2,4]triazole;

3-methyl-3-(1-methoxycarbonyl-2-methoxyethen-1-yl)-6-phenyl-3H-imidazo[1,2-b][1,2,4]triazole.

One example of the possible isomerisms of the compounds of general formula (I) is the isomerism of the double bond contained in the groups of general formula (II) or (III) which define the substituent T:

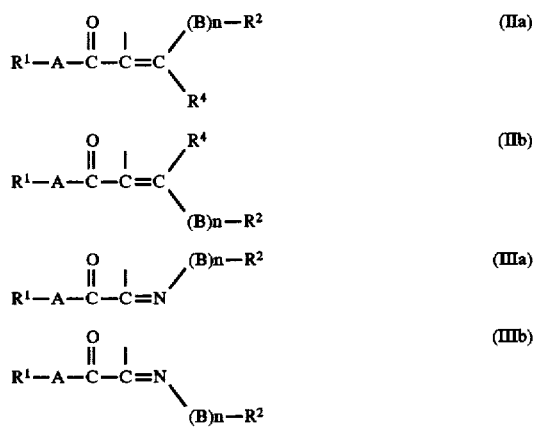

The compounds of general formula (I) according to the present invention can be prepared by numerous synthetic paths, illustrated in the ensuing Schemes 1–12, in which unless otherwise stated the symbols used have the meanings already defined for the compounds of general formula (I). Moreover, for greater clarity all the preparation processes for said compounds are illustrated by the synthesis of particular cases of the compounds of general formula (I), the described method however being generally applicable to all compounds of general formula (I), the only exceptions being those stated in the description.

If X represents a sulphur or oxygen atom or an —N(R)— group in which R has the aforestated meaning, and K, Y, Q, W and Z have the aforestated meaning, the compounds of general formula (I) can be represented by the general formula (IA):

and can be prepared for example from compounds of general formula (Ip1)

in which X, Y, K, Q, W and Z have the aforesaid meaning for the compounds of formula (IA), with the exception of the substituent T which can be defined as a group of general formula (VII):

in which A has the aforesaid meaning and $R^{11}$ can have the same aforesaid meaning as $R^1$, or can represent a group of general formula (VIII):

where $R^1$, $R^5$, $R^6$ and A have the aforesaid meanings. The condition that at least one of the said groups X, Y, K, Q, W and Z contains a T group is maintained valid. By one of the methods illustrated in Schemes 1–5 the group (VII) can be transformed into one of the groups (II), (III), (IV) and (V) which define T in the compounds of general formula (I) in the particular case in which B represents an oxygen atom and n is 1.

Scheme 1 proposes the synthesis of a compound of general formula (Ia111), which is obtained when T represents a group of general formula (II) in the particular case in which B is oxygen and n is 1.

SCHEME 1

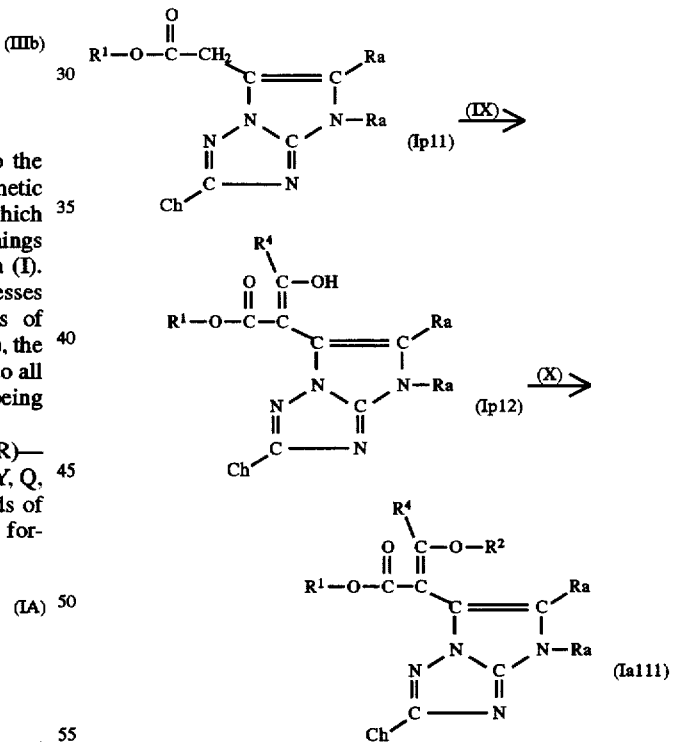

The method of Scheme 1 comprises reacting the acetate of general formula (Ip11) with an alkyl alkanoate of general formula (IX):

in which $R^{12}$ represents a $C_1$–$C_4$ alkyl group, in a dipolar aprotic solvent such as N,N-dimethylformamide or N-methylpyrrolidone, or in an aromatic solvent such as benzene or toluene, or in an ether solvent such as diethyl ether, tetrahydrofuran or dioxane, or in an alcoholic solvent such as methanol, ethanol or propanol, in the presence of a base such as sodium hydride, sodium methylate or potassium t-butylate, at a temperature of between −10° C. and the boiling point of the solvent, to obtain the salt of general formula (Ip12) from which, by reaction with a halogenating agent of general formula (X):

in which [Halo] represents a halogen atom such as chlorine, bromine or iodine, or with a suitable sulphonic ester or with a dialkylsulphate such as methyl p-toluenesulphonate, propyl methanesulphonate, dimethylsulphate or diethylsulphate, and operating in the same reaction environment at a temperature of between −10° C. and 40° C., the desired compound of general formula (Ia111) is obtained.

Scheme 2 proposes the synthesis of a compound of general formula (Ia112), which is obtained when T represents a group of general formula (III) in the particular case in which B is oxygen and n is 1.

SCHEME 2

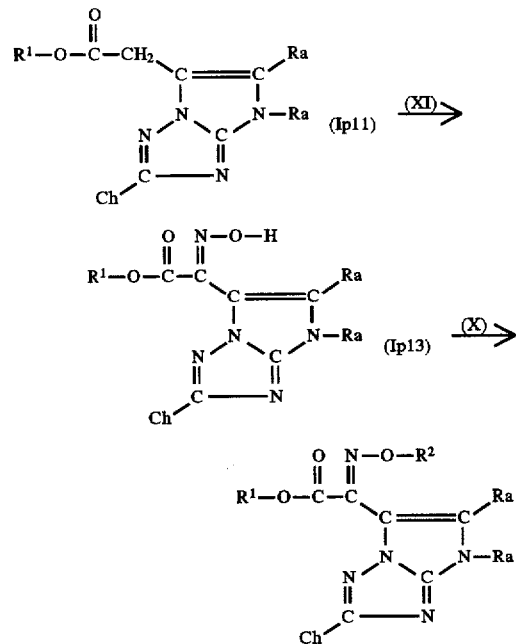

The method of Scheme 2 comprises reacting the acetate of general formula (Ip11) with an alkyl nitrite of general formula (XI):

in which $R^{13}$ represents a $C_1$–$C_4$ alkyl group in an ether solvent such as diethyl ether, tetrahydrofuran or dioxane, or in an alcoholic solvent such as methanol, ethanol or propanol, in the presence of a base such as sodium hydride, sodium methylate or potassium t-butylate, at a temperature of between −10° C. and the boiling point of the solvent, to obtain the salt of general formula (Ip13) from which, by reacting with a halogenating agent of the aforesaid general formula (X), or with a suitable sulphonic ester or with a dialkylsulphate such as methyl p-toluenesulphonate, propyl methanesulphonate, dimethylsulphate or diethylsulphate, operating in the presence of an ether or alcoholic solvent chosen from the aforesaid and a base such as potassium carbonate or sodium methoxide at a temperature of between −10° C. and 40° C., the desired compound of general formula (Ia112) is obtained.

Scheme 3 proposes the synthesis of a compound of general formula (Ia113), which is obtained when T represents a group of general formula (IV).

SCHEME 3

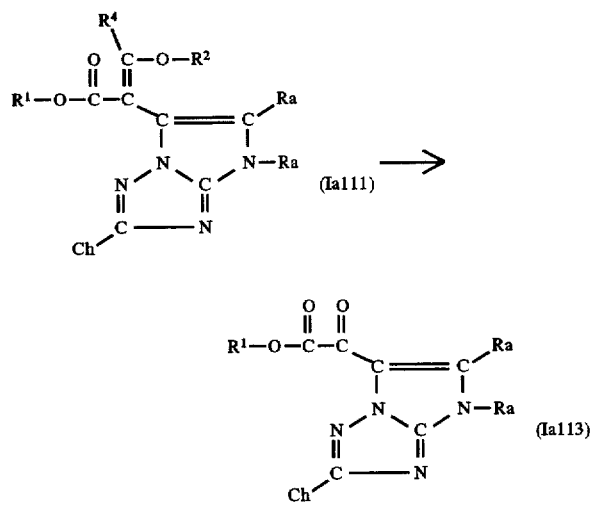

The method of Scheme 3 comprises ozonolysis, by the procedure described for example in European patent No. 331,061, of the compound of general formula (Ia111) obtained by the method described in Scheme 1.

Scheme 4 proposes the synthesis of a compound of general formula (Ia114), which is obtained when T represents a group of general formula (V) in the particular case in which B is oxygen and n is 1.

SCHEME 4

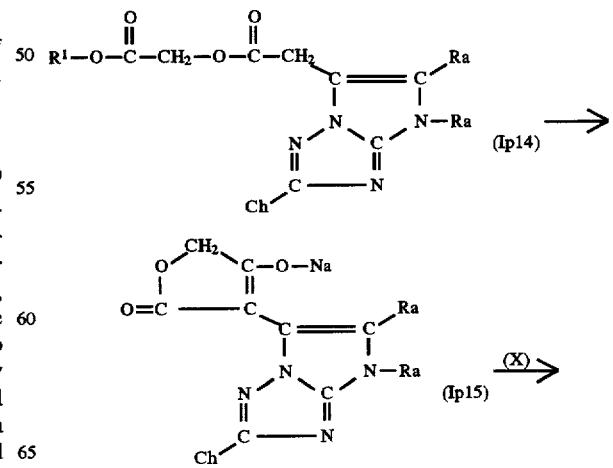

-continued
SCHEME 4

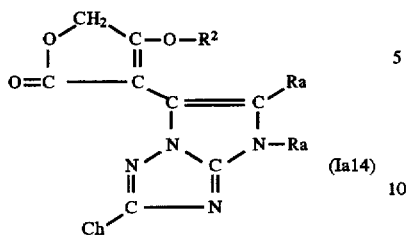
(Ia14)

The method of Scheme 4 comprises cyclizing the ester of general formula (Ip14) easily obtained from the aforesaid acetate of general formula (Ip11) by saponifying the ester group, followed by reacting with a bromo acetate of general formula (XII):

  (XII)

in the presence of a base such as potassium carbonate, potassium fluoride or triethylamine, at a temperature of between 0° C. and 40° C., in the presence of a dipolar aprotic solvent such as N,N-dimethylformamide or N-methylpyrrolidone, in the presence of a base such as sodium hydride, or potassium t-butylate, at a temperature of between −10° C. and 80° C., to obtain the salt of general formula (Ip15) from which, by reacting with a halogenating agent of the aforesaid general formula (X), operating in the presence of a solvent chosen from the aforesaid at a temperature of between −10° C. and 40° C., the desired compound of general formula (Ia114) is obtained.

If the substituent T is represented by the group of general formula (II), the compounds of general formula (Ip1) can also be conveniently transformed into the compounds of general formula (I) according to the present invention by the method illustrated in Scheme 5 in those cases in which n is 1 and B represents oxygen (Id121), or sulphur (Id122), or an —N(R³)— group (Id123).

SCHEME 5

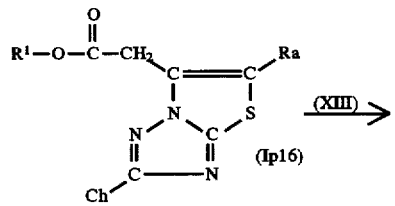
(Ip16)

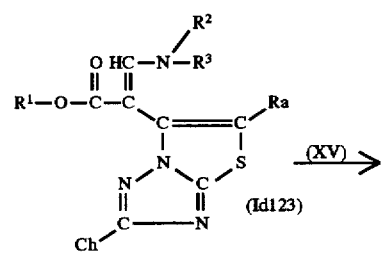
(Id123)

-continued
SCHEME 5

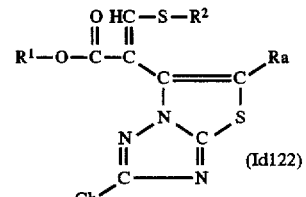
(Id122)

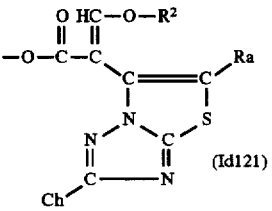
(Id121)

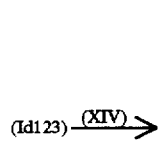
(Id123)

The method of Scheme 5 comprises reacting the acetate of general formula (Ip16) which is easily transformed into the corresponding silylether by reaction with a silylating agent such as trimethylsilylchloride, with an amino-orthoester of general formula (XIII):

$$(R^{14}O)_2NR^2R^3CH \quad (XIII)$$

in which $R^{14}$ represents a $C_1$–$C_4$ alkyl group, in the presence of a Lewis acid such as titanium tetrachloride at a temperature of between −30° C. and 40° C., to obtain the desired compound of formula (Id123). The compound (Id123) is easily converted into the compound (Id121) by treatment with a solution of hydrochloric acid in an alcohol of general formula (XIV):

$$R^2\text{—OH} \quad (XIV)$$

at a temperature between ambient and the boiling point of the alcohol; or alternatively into the compound (Id122) by treatment with a sulphide of general formula (XV):

$$R^2\text{—SH} \quad (XV)$$

in the presence of Lewis acids such as mercury chloride or boron trifluoride, or bases such as potassium carbonate, at a temperature of between 0° C. and 100° C.

A further method useful for preparing the compounds of general formula (I) according to the present invention, in the case in which the substituent T is represented by a group of general formula (II), (III) or (IV), is that shown in Scheme 6.

SCHEME 6

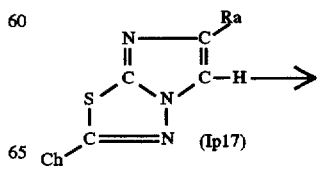
(Ip17)

-continued
SCHEME 6

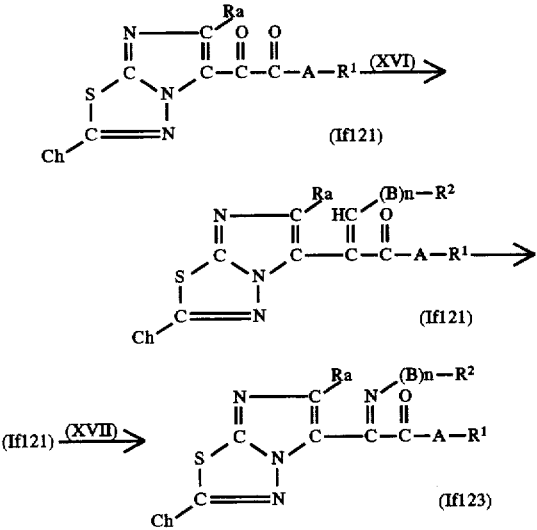

The method of Scheme 6 comprises transforming the compound of general formula (Ip17), by the method described hereinafter in Scheme 10, into the compound of general formula (If121) which is transformed, by reaction with a phosphonium salt of general formula (XVI):

$$(Ph)_3P^+—CH_2—(B)_n—R^2Br^- \qquad (XVI)$$

in the presence of a base such as sodium hydride or potassium t-butylate and a dipolar aprotic solvent such as dimethylsulphoxide, or an ether solvent such as diethyl ether or tetrahydrofuran, at a temperature of between –30° C. and 40° C., into the desired compound of general formula (If122). The compound (If121) can also be transformed into the compound (If123) by treatment with a suitable amino derivative, either as the free base or salified with acids such as hydrochloric acid or sulphuric acid, of general formula (XVII):

$$H_2N—(B)_n—R_2 \qquad (XVII)$$

in the presence of alcoholic solvents such as methanol or ethanol, under neutral or acid catalysis conditions, at a temperature of between 25° C. and 80° C.

The compounds of general formula (Ip1) can be obtained, according to the meaning of X, Y, K, Q, W and Z, by methods described in the literature, such as in: "Journal of Chemical Society" (1976), pp. 1225–1228; "Journal of Heterocyclic Chemistry" (1978), Vol. 15, pp. 401–411; "Journal of Heterocyclic Chemistry" (1980), Vol. 17, pp. 1321–1323; "Journal of Organic Chemistry" (1984), Vol. 49, p 3534; "Chemical Berichte" (1987), Vol. 120, p. 965; in European patent application No. 427,248; in U.S. Pat. No. 5,055,587; and by Katrinsky A., Rees C. in "Comprehensive Heterocyclic Chemistry" (1984), Vol. 1–6, Pergamon Press Publ.

Some methods are described hereinafter by way of example for preparing compounds of general formula (Ia):

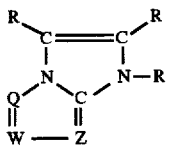

falling within the compounds of general formula (I) in the case in which X represents an —N(R)— group; Y and K represent the =C(R)— group; and Q, W and Z are defined as in general formula (I). Particular cases of compounds of general formula (Ia) are shown by way of example in Schedule 1 (Compounds Ia1–Ia4). These can be prepared by the method described in Scheme 1, via synthesis of a compound of general formula (Ip11) which falls within the compounds of general formula (Ip1) and is then transformed into the desired compound (Ia11) by operating in accordance with the conditions described in Schemes 1–5.

SCHEME 7

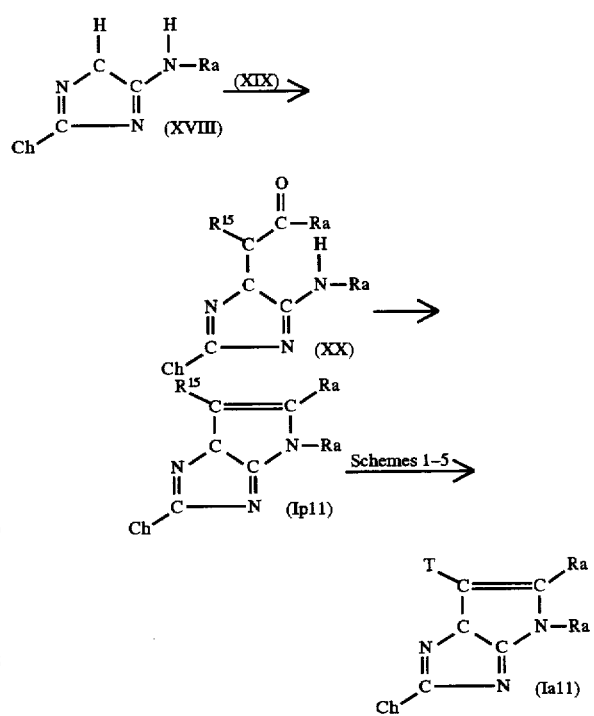

The method of Scheme 7 comprises reacting the aminotriazole of general formula (XVIII), obtained by the methods described in the literature, such as in "Journal of Chemical Society Perkin II" (1973), pp. 2047–2054; "Bulletin de la Societé Chimique France" (1975), pp. 1649–1653; and by Temple C., Montgomery J. A. in "The Chemistry of Heterocyclic Compounds" (1984), "Triazoles"; John Wiley & Sons Publ.; with an α-bromoketone of general formula (XIX):

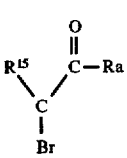

in which $R^{15}$ represents a group (VII) with the aforesaid meaning, in a dipolar aprotic solvent such as N,N-dimethylformamide, or in an alcoholic solvent such as methanol, ethanol or propanol, or in water, in the presence of a base such as potassium carbonate or caustic potash at a temperature of between 5° C. and 40° C., to obtain the compound of general formula (XX) which is cyclized in an alcoholic solvent chosen from the aforesaid, or in water, at a temperature which depends on the nature of the solvents used and in any event between 60° C. and 180° C., to obtain the compound of general formula (Ip11). The desired compound of general formula (Ia) is obtained from the compound (Ip11) by transforming the group $R^{15}$ into one of the T groups by operating in the manner described in Schemes 1–5.

A description is also given of the synthesis of compounds of general formula (Ib):

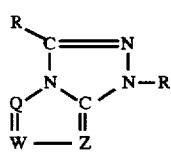
(Ia)

which fall within the compounds of general formula (I) in the case in which X represents an —N(R)— group; Y represents an =N— group; K represents a =C(R)— group; and Q, W and Z are defined as in general formula (I). Particular cases of compounds of formula (Ib) are shown by way of example in Schedule 1 (Compounds Ib1–Ib4). They can be prepared by the method described in Scheme 8, via the synthesis of a compound of general formula (Ip18) falling within the compounds of general formula (Ip1), which is then transformed into the desired compound (Ib11) by operating in accordance with the conditions described in Schemes 1–5.

SCHEME 8

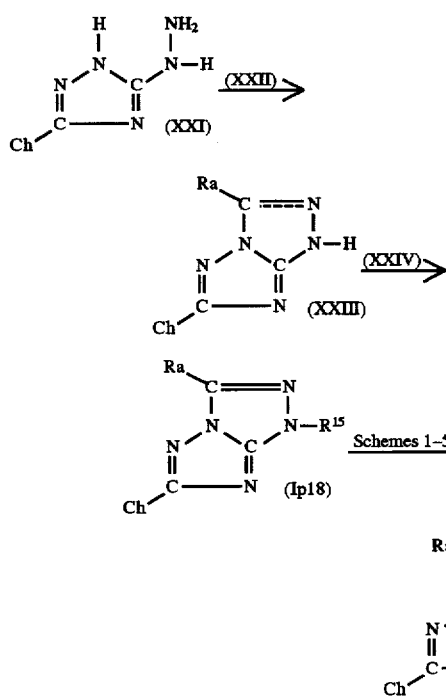

The method of Scheme 8 comprises reacting the triazole of general formula (XXI) obtained by the methods described in the literature, for example in "Organic Synthesis Collection", Vol. 1, p. 422; "Journal of Chemical Society" (1971), p. 167; and in European patent application No. 487,081; with an iminoester of general formula (XXII):

(XXII)

in which $R^{16}$ represents a $C_1C_3$ alkyl group, in an alcoholic solvent such as methanol, ethanol or propanol, at a temperature of between ambient and the boiling point of the solvent, to obtain the compound of general formula (XXIII) which is alkylated with a haloester of general formula (XXIV):

$R^{15}$-[Halo]  (XXIV)

in which $R^{15}$ and Halo have the aforesaid meaning, in a dipolar aprotic solvent such as N,N-dimethylformamide, or in an alcoholic solvent such as ethanol, at a temperature between 0° C. and the boiling point of the solvent, to obtain the compound of general formula (Ip18). The desired compound of general formula (Ib) is obtained from the compound (Ip18) by transforming the group $R^{15}$ into one of the T groups by operating in the manner described in Schemes 1–5.

A description is also given of the synthesis of compounds of general formula (Ide):

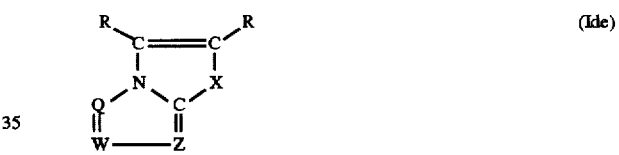
(Ide)

which fall within the compounds of general formula (I) in the case in which X represents an oxygen or sulphur atom; Y and K represent a =C(R)— group; and Q, W and Z are defined as in general formula (I). Particular cases of compounds of formula (Ide) are shown by way of example in Schedule 1 (Compounds Id1–Id4 and Ie1–Ie4). They can be prepared by the method described in Scheme 9, via the synthesis of a compound of general formula (Ip19) which is then transformed into the desired compound (Id12) by operating in accordance with the conditions described in Schemes 1–5.

SCHEME 9

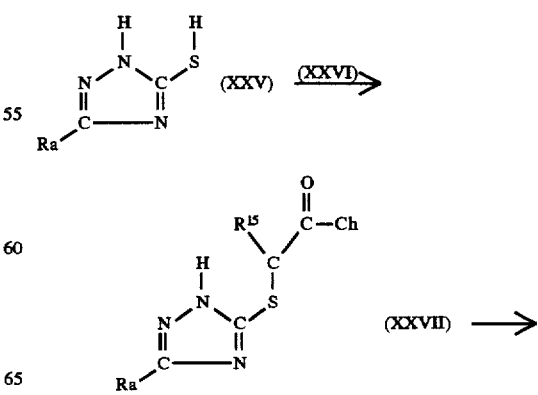

-continued
SCHEME 9

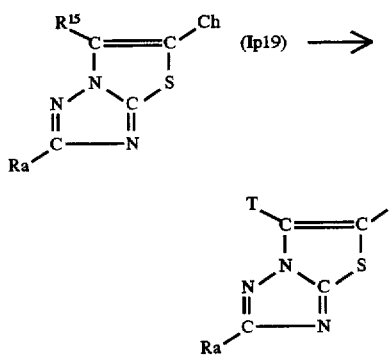

The method of Scheme 9 comprises reacting thiotriazole of general formula (XXV) obtained by methods described in the literature, for example in "Journal of Heterocyclic Chemistry" (1978), Vol. 15, pp. 401–411, with a haloketone of general formula (XXVI) or with the corresponding ketal:

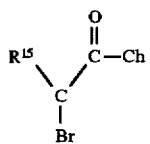

(XXVI)

in which $R^{15}$ has the aforesaid meaning, in an alcoholic solvent such as methanol, ethanol or propanol, or in a mixture of solvents such as water and tetrahydrofuran, in the presence of a base such as sodium acetate or triethylamine, at a temperature of between ambient and the boiling point of the solvent, to obtain the compound of general formula (XXVII) which is cyclized by heating in an alcoholic solvent such as ethanol in the presence of strong acids such as hydrochloric acid, at a temperature of between 60° C. and the boiling point of the solvent, to obtain the compound of general formula (Ip19). The desired compound of general formula (Id12) is obtained from the compound (Ip19) by transforming the group $R^{15}$ into one of the T groups by operating in the manner described in Schemes 1–5.

As an example of the synthesis of compounds of general formula (I) where T represents a group of general formula (IV), Scheme 10 shows the preparation of compounds of general formula (If1).

SCHEME 10

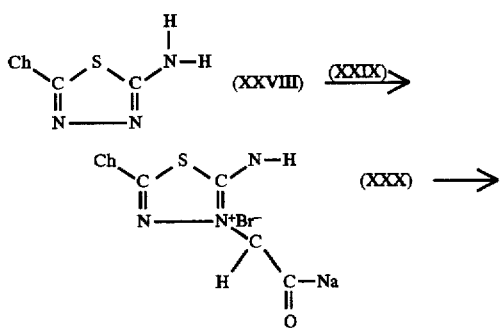

-continued
SCHEME 10

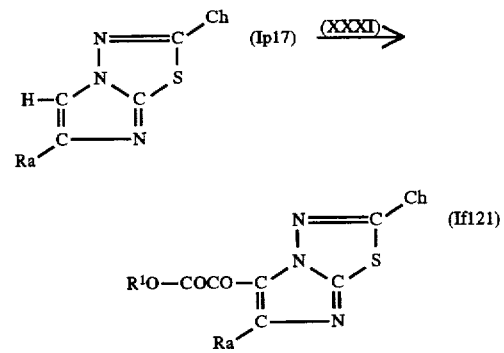

The method of Scheme 10 comprises reacting aminothiadiazole of general formula (XXVIII) obtained by methods described in the literature, for example in "Journal Heterocyclic Chemistry" (1984), Vol. 22, p. 361, with a halide of general formula (XXVIII):

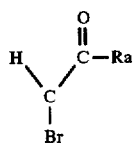

(XXVIII)

in a polar solvent such as acetone, ethylmethylketone or diethyl ether, at ambient temperature, to obtain the compound of general formula (XXX). The compound of general formula (XXX) is cyclized by heating in a protic solvent such as water or ethanol, or in a dipolar aprotic solvent such as N,N-dimiethylformamide, at a temperature of between 70° C. and the boiling point of the solvent used, to obtain the compound of general formula (Ip17). The desired compound of general formula (If121) is obtained from the compound (Ip17) by acylation by heating to a temperature of between 0° C. and 60° C. in the presence of a chloride of general formula (XXXI):

$$Cl-COCO-OR^1 \quad (XXXI)$$

in a halogenated solvent such as dichloromethane or dichloroethane. The compound of general formula (If121) can be easily transformed into compounds of general formula (If12) by the reactions previously described in Scheme 6.

When K represents an —N(R)— group in which R has the aforesaid meaning, and X, Y, Q, W and Z have the aforesaid meanings, the compounds of general formula (I) can be represented by the general formula (IB):

and can be obtained by the method described in Scheme 11 for the synthesis of a compound of general formula (Ih111). Examples of derivatives of general formula (IB) are illustrated in Schedule 1 (Compounds Ih1–Ih4).

SCHEME 11

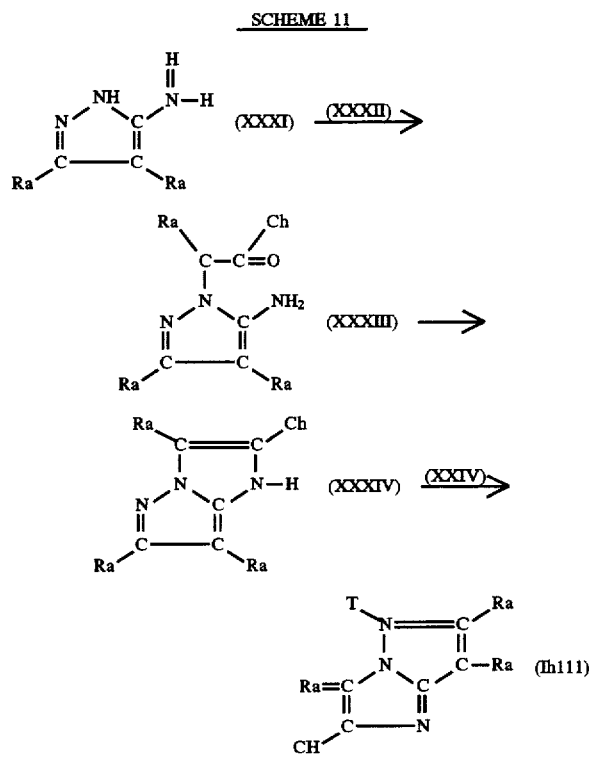

The method of Scheme 11 comprises reacting aminopyrazole of general formula (XXXI) obtained by methods described in the literature, for example in U.S. Pat. No. 5,089,651, with a bromoketone of general formula (XXXII):

in a dipolar aprotic solvent such as N,N-dimethylformamide, in the presence of a base such as potassium carbonate, at ambient temperature to obtain the compound of general formula (XXXIII) which is cyclized by heating in a dipolar aprotic solvent such as N,N-dimethylformamide or in a protic solvent such as water or ethyl alcohol or in an aromatic solvent such as toluene, at a temperature of between 40° C. and the boiling point of the solvent, to obtain the compound of general formula (XXXIV). The desired compound of general formula (Ih111) is obtained from the compound (XXXIV) by alkylation, with the aforesaid haloester of general formula (XXIV), in a dipolar aprotic solvent such as N,N-dimethylformamide, in the presence of a base such as potassium carbonate, at a temperature of between 20° C. and 80° C.

When K and Y represent an =N— group or a =C(R)— group, and X represents one of the following groups: —N=C(R)—, —C(R)=C(R)—, —C(R)=N—, in which R has the aforesaid meaning, the compounds of general formula (I1) can be easily obtained by the method described in Scheme 12. Examples of derivatives of general formula (I1) are illustrated in Schedule 1 (Compounds I11–I12).

SCHEME 12

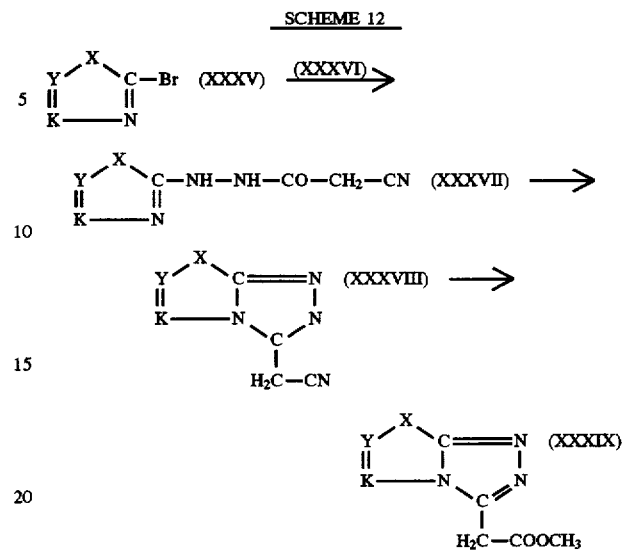

The method of Scheme 12 comprises reacting the heterocyclic bromide of general formula (XXXV) with a hydrazide of general formula (XXXVI):

$$NH_2-NH-CO-CH_2-CN \qquad (XXXVI)$$

in a dipolar aprotic solvent such as N,N-dimethylacetamide or N-methylpyrrolidone, or in an alcoholic solvent such as ethanol or propanol, at a temperature of between ambient and the solvent reflux temperature, to obtain the compound of general formula (XXXVII). The compound of general formula (XXXVII) obtained in this manner is reacted with tetrachloromethane or with tetrabromomethane in the presence of triphenylphosphine, in acetonitrile as solvent, at a temperature of between −10° C. and 100° C., to obtain the compound of general formula (XXXVIII) which is converted into the corresponding methanolic ester of general formula (XXXIX) by treatment with a solution of hydrochloric acid in methanol, at a temperature of between 0° C. and the boiling point of the solvent. The desired compound of general formula (I1) is obtained from the compound of general formula (XXXIX) by one of the methods illustrated in Schemes 1–5.

The intermediates used can all be prepared by methods described in the art.

The heterocyclic compounds can be prepared as described for example by Katrinsky A., Rees C. in "Comprehensive Heterocyclic Chemistry" (1984), Vol. 1–6, Pergamon Press Publ.

The haloketones are generally commercial products.

The compounds of general formula (I) possess particularly high fungicidal activity against fungal pathogens of various kinds. They are particularly effective against sugarbeet, cereal, Cucurbitaceae and fruit tree fungi. They can also be active as antimycotics, for example for controlling pathogenic fungi pertaining to the genus Candida or the genus Trichophytum.

The plant diseases which can be combated with the compounds of the present invention include for example the following:

*Helminthosporium teres* on cereals;
*Erysiphe graminis* on cereals;
*Puccinia spp.* on cereals;

*Plasmopara viticola* on vines;
Phytium on vegetables;
*Phytophthora spp.* on vegetables;
*Septoria spp.* on cereals;
*Sphaerotheca fuliginea* on Cucurbitaceae (eg. cucumber);
Rhynchosporium on cereals;
*Podosphaera leucotricha* on apple trees;
*Uncinula necator* on vines;
*Venturia spp.* on fruit trees;
*Pyricularia oryzae* on rice;
*Botrytis cinerea*;
*Fusarium spp.* on cereals; etc.

When used for phytoiatric purposes, the compounds of general formula (I) exhibit a fungicidal action which is both curative and preventive, and in addition exhibit only low or no phytotoxicity. For practical uses in agriculture it is often useful to have available fungicidal compositions containing as active substance one or more compounds of general formula (I), possibly as an isomer mixture.

These compositions can be applied to all parts of the plant, for example onto leaves, stalks, branches and roots, or onto the seeds themselves before sowing, or onto the ground in which the plant is growing.

Compositions can be used in the form of dry powders, wettable powders, emulsifiable concentrates, microemulsions, pastes, granulates, solutions, suspensions etc. The choice of the type of composition depends on the specific use.

The compositions are prepared by known methods, for example by diluting or dissolving the active substance in a solvent medium and/or a solid diluent, possibly with surfactants present.

The following can be used as solid diluents or supports: silica, kaolin, bentonite, talc, diatomaceous earth, dolomite, calcium carbonate, magnesia, chalk, clays, synthetic silicates, attapulgite, sepiolite.

In addition to water, liquid diluents can comprise various types of solvent, such as aromatic (xylols or alkylbenzene mixtures), chloroaromatic (chlorobenzene), paraffin (petroleum fractions), alcohol (methanol, propanol, butanol, octanol, glycerin), amine, amide (N,N'-dimethylformamide, N-methylpyrrolidone), ketone (acetone, cyclohexanone, acetophenone, isophorone, ethylamylketone), ester (isobutyl acetate).

Surfactants can include sodium salts, calcium salts, triethanolamine salts, alkylsulphates, alkylarylsulphonates, alkylphenol polyethoxylates, fatty acids condensed with ethylene oxide, polyoxyethylene fatty acids, polyoxyethylene sorbitol esters, and ligninsulphonates.

The compositions can also contain special additives for particular purposes, for example adhesivating agents such as gum arabic, polyvinylalcohol or polyvinylpyrrolidone.

Other compatible active substances can also be added to the compositions of the present invention if desired, such as fungicides, phytoregulators, antibiotics, herbicides, insecticides or fertilizers.

The active substance concentration in said compositions can vary within a wide range, depending on the active compound, the culture, the pathogen, the environmental conditions and the type of formulation used.

In general the active substance concentration varies from 0.1% to 95%, preferably from 0.5% to 90%.

The following examples are given as non-limiting illustration of the present invention.

EXAMPLE 1

Preparation of 2-t-butyl-5-(methoxyiminomethoxycarbonylmethyl)-6-methylimidazolo[2,1-b]-1,3,4-thiadiazole
(Compound No. 1)

a) A solution of 10.4 g of methyloxalylchloride in 10 cm³ of sym-dichloroethane is dripped into a solution of 11.5 g of 2-t-butyl-6-methylimidazolo[2,1-b]-1,3,4-thiadiazole in 50 cm³ of sym-dichloroethane cooled to 0° C.

The solution is heated to 60° C. for 3 hours under reflux, is then cooled and is poured into 120 cm³ of brine at a temperature of 10° C.

The organic phase is separated, washed with 100 cm³ of water, dried over sodium sulphate and evaporated under reduced pressure. 15 g of 2-t-butyl-5-methoxycarbonyloxymethyl-6-methylimidazolo-[2,1-b]-1,3,4-thiadiazole with a yield of 91% are obtained, suitable for use directly in the next reaction b).

b) 15 g of 2-t-butyl-5-methoxy-carbonyloxy-methyl-6-methylimidazolo-[2,1-b]-1,3,4-thiadiazole are added to a solution of 4.2 g of N-methylhydroxylamine hydrochloride and 3.2 g of sodium acetate in 100 cm³ of methanol.

After 3 hours of agitation at ambient temperature, the solution is evaporated and the residue is taken up in ethyl acetate. The solution obtained is washed twice with water, dried over sodium sulphate and evaporated under reduced pressure.

The impure residue obtained is purified by silica gel chromatography using as eluent a 3/7 ethyl acetate/hexane mixture. 6 g of E isomer and 5 g of Z isomer of compound No. 1 are obtained with an overall yield of 66%, its structure being deducible from Table 1.

Table 2 shows the elemental analysis.

EXAMPLE 2

Preparation of 2-t-butyl-5-(1-methoxycarbonyl-2-methoxyethen-1-yl)-6-methylimidazolo[2,1-b]-1,3,4-thiadiazole (Compound No. 2)

9 g of potassium t-butylate are added at ambient temperature to a solution of 28 g of triphenylmethoxymethylphosphonium bromide in 200 cm³ of dioxane. After 2 hours a solution of 4.5 g of 2-t-butyl-5-methoxycarbonyloxymethyl-6-methylimidazolo-[2,1-b]-1,3,4-thiadiazole in 20 cm³ of dioxane is added by dropping. The resultant solution is left under agitation at 20° C. for 1 hour and then refluxed for 4 hours.

The solution is left overnight under agitation at ambient temperature and is then poured into an ammonium chloride solution and extracted twice with ethyl acetate.

The organic phases obtained are pooled, washed with water, dried over sodium sulphate and evaporated under reduced pressure.

The impure residue obtained is purified by silica gel chromatography using as eluent a 4/6 ethyl acetate/hexane mixture. 2.7 g of E isomer and 1.8 g of Z isomer of compound No. 2 are obtained with an overall yield of 90%, its structure being deducible from Table 1.

Table 2 shows the elemental analysis.

EXAMPLE 3

Preparation of 2-(4-methoxyphenyl)-5-(1-methoxycarbonyl-2-methoxyethen-1-yl)-6-methylimidazolo[2,1-b]-1,3,4-thiadiazole
(Compound No. 4)

A solution of 10 g of 2-(4-methoxyphenyl)-5-methoxycarbonylmethyl-6-methylimidazolo-[2,1-b]-1,3,4-thiadiazole in 50 cm³ of methyl formate is dripped into a solution of 1.8 g of sodium hydride bromide in 10 cm³ of anhydrous dimethylformamide (DMF). The solution is left under agitation overnight at ambient temperature and is then poured into water and extracted twice with ethyl acetate.

The organic phases obtained are pooled, dried over sodium sulphate and evaporated under reduced pressure.

The impure residue obtained is purified by silica gel chromatography using as eluent a 3/7 ethyl acetate/hexane mixture. 8.9 g of E isomer and 0.9 g of Z isomer of compound No. 4 are obtained with an overall yield of 87%, its structure being deducible from Table 1.

Table 2 shows the elemental analysis.

EXAMPLES 4–16

Operating with procedures analogous to those described in Examples 1–3, the following compounds Nos. 3 and 5–16 were prepared, their structure being deducible from Table 1.

Table 2 shows the elemental analysis.

Compound No. 3:

2-(4-methoxyphenyl)-5-(methoxyiminomethoxycarbonylmethyl)-6-methylimidazolo[2,1-b]-1,3,4-thiadiazole.

Compound No. 5:

2-(4-methoxyphenyl)-5-(1-methoxycarbonyl-2-ethylethen-1-yl)-6-methylimidazolo[2,1-b]-1,3,4-thiadiazole.

Compound No. 6:

2-(4-methoxyphenyl)-5-(1-N-methylcarbamoyl-2-methoxyethen-1-yl)-6-methylimidazolo[2,1-b]-1,3,4-thiadiazole.

Compound No. 7:

6-(4-chlorophenyl)-5-(1-methoxycarbonyl-2-methoxyethen-1-yl)-thiazolo[2,3-c]-1,3,4-triazole.

Compound No. 8:

2,3-dimethyl-6-(4-methoxyphenyl)-1-(1-methoxycarbonyl-2-methoxyethen-1-yl)-3H-imidazolo[1,2-b][1,2,4]triazole.

Compound No. 9:

2-methyl-6-(4-methoxyphenyl)-3-(1-methoxycarbonyl-2-methoxyethen-1-yl)-3H-imidazolo[1,2-b]pyrazole.

Compound No. 10:

2-methyl-5-(1-methoxycarbonyl-2-methoxyethen-1-yl)-6-phenylthiazolo[3,2-b]-[1,2,4]-triazole.

Compound No. 11:

2-methyl-5-phenoxymethyl-6-(1-methoxycarbonyl-2-methoxyethen-1-yl)-thiazolo[3,2-b]-[1,2,4]-triazole.

Compound No. 12:

2-methyl-5-(4-chlorophenoxy)methyl-6-(1-methoxycarbonyl-2-methoxyethen-1-yl)-thiazolo[3,2-b]-[1,2,4]-triazole.

Compound No. 13:

5-(4-chlorophenoxy)methyl-6-(1-methoxycarbonyl-2-methoxyethen-1-yl)-thiazolo[3,2-b]-[1,2,4]-triazole.

Compound No. 14:

2-trifluoromethyl-5-(4-chlorophenoxy)methyl-6-(1-methoxycarbonyl-2-methoxyethen-1-yl)-thiazolo[3,2-b]-[1,2,4]-triazole.

Compound No. 15:

2-trifluoromethyl-5-(4-chlorophenoxy)methyl-6-(1-methoxycarbonyl-2-methoxyethen-1-yl)-imidazolo[2,1-b]-1,3,4-thiadiazole.

Compound No. 16:

2-methyl-3-(1-methoxycarbonyl-2-methoxyethen-1-yl)-5-methyl-6-(4-chlorophenoxy)methyl-imidazolo[2,1-b]-thiazole.

EXAMPLE 17

Determination of preventive fungicidal activity against cucumber oidium (*Sphaerotheca fuliginea*)

Leaves of cucumber cultivar Marketer plants, grown in pots in an air conditioned environment (20±1° C., 70% relative humidity), are treated by spraying both leaf faces with the compounds Nos. 1–16 in a 20 vol % acetone solution in water.

After 24 hours in the air conditioned environment the plants were sprayed on both leaf faces with an aqueous suspension of *Sphaerotheca fuliginea* conidia (200000 conidia per $cm^3$).

The plants are kept in a moisture-saturated environment at 21° C. for the fungus incubation period.

At the end of this period (8 days) the fungicidal activity is evaluated on a percentage evaluation scale from 100 (healthy plant) to 0 (plant completely infected).

All the synthesized compounds showed control exceeding 90 at a concentration of 500 ppm.

EXAMPLE 18

Determination of preventive fungicidal activity against barley helminthosporiosis (*Helminthosporium teres*)

Leaves of barley cultivar Arna plants, grown in pots in an air conditioned environment (20±1° C., 70% relative humidity), are treated by spraying both leaf faces with the compounds Nos. 1–16 in a 20 vol % acetone solution in water.

After 24 hours in the air conditioned environment the plants were sprayed on both leaf faces with an aqueous suspension of *Helminthosporium teres* conidia (250000 conidia per $cm^3$).

The plants are kept in a moisture-saturated environment at 21° C. for the fungus incubation period.

At the end of this period (12 days) the fungicidal activity is evaluated on a percentage evaluation scale from 100 (healthy plant) to 0 (plant completely infected).

All the synthesized compounds showed control exceeding 90 at a concentration of 500 ppm.

EXAMPLE 19

Determination of preventive fungicidal activity against vine peronospora (*Plasmopara viticola*)

Leaves of vine cultivar Dolcetto plants, grown in pots in an air conditioned environment (20±1° C., 70% relative humidity), are treated by spraying both leaf faces with the compounds Nos. 1–16 in a 20 vol % acetone solution in water.

After 24 hours in the air conditioned environment the plants were sprayed on both leaf faces with an aqueous suspension of *Plasmopora viticola* conidia (200000 conidia per $cm^3$).

The plants are kept in a moisture-saturated environment at 21° C. for the fungus incubation period.

At the end of this period (7 days) the fungicidal activity is evaluated on a percentage evaluation scale from 100 (healthy plant) to 0 (plant completely infected).

All the synthesized compounds showed control exceeding 90 at a concentration of 500 ppm.

TABLE 1

Examples of compounds of general formula (I)

| COMPOUND NO. | X | Y | K | Q | W | Z | T |
|---|---|---|---|---|---|---|---|
| 1 | —S— | =C(Ch)— | =N— | =C(T)— | =C(Ra)— | =N— | (III) |
| 2 | —S— | =C(Ch)— | =N— | =C(T)— | =C(Ra)— | =N— | (II) |
| 3 | —S— | =C(Ch)— | =N— | =C(T)— | =C(Ra)— | =N— | (III) |
| 4 | —S— | =C(Ch)— | =N— | =C(T)— | =C(Ra)— | =N— | (II) |
| 5 | —S— | =C(Ch)— | =N— | =C(T)— | =C(Ra)— | =N— | (II) |
| 6 | —S— | =C(Ch)— | =N— | =C(T)— | =C(Ra)— | =N— | (II) |
| 7 | —S— | =C(Ch)— | =C(T)— | =N— | =C(Ra)— | =N— | (II) |
| 8 | —N(CE)$_3$— | =C(Ra)— | =C(T)— | =N— | =C(Ch)— | =N— | (II) |
| 9 | —N(T)— | =C(Ra)— | —CE= | =N— | =C(Ch)— | =CE— | (II) |
| 10 | —S— | =C(Ch)— | =C(T)— | =N— | =C(Ra)— | =N— | (II) |
| 11 | —S— | =C(T)— | =C(Ch)— | =N— | =C(Ra)— | =N— | (II) |
| 12 | —S— | =C(T)— | =C(Ch)— | =N— | =C(Ra)— | =N— | (II) |
| 13 | —S— | =C(T)— | =C(Ch)— | =N— | =C(Ra)— | =N— | (II) |
| 14 | —S— | =C(T)— | =C(Ch)— | =N— | =C(Ra)— | =N— | (II) |
| 15 | —S— | =C(Ra)— | =N— | =C(Ch)— | =C(T)— | =N— | (II) |
| 16 | —S— | =C(Ra)— | =C(T)— | =C(Ra)— | =C(Ch)— | =N— | (II) |

| COMPOUND NO. | A | B | n | $R_1$ | $R_2$ | $R_a$ | Cb |
|---|---|---|---|---|---|---|---|
| 1 | —O— | —O— | 1 | methyl | methyl | methyl | t-butyl |
| 2 | —O— | —O— | 1 | methyl | methyl | methyl | t-butyl |
| 3 | —O— | —O— | 1 | methyl | methyl | methyl | 4-methoxyphenyl |
| 4 | —O— | —O— | 1 | methyl | methyl | methyl | 4-methoxyphenyl |
| 5 | —O— | — | 0 | methyl | ethyl | methyl | 4-methoxyphenyl |
| 6 | —NE— | —O— | 1 | methyl | methyl | methyl | 4-methoxyphenyl |
| 7 | —O— | —O— | 1 | methyl | methyl | hydrogen | 4-chlorophenyl |
| 8 | —O— | —O— | 1 | methyl | methyl | methyl | 4-methoxyphenyl |
| 9 | —O— | —O— | 1 | methyl | methyl | methyl | 4-methoxyphenyl |
| 10 | —O— | —O— | 1 | methyl | methyl | methyl | phenyl |
| 11 | —O— | —O— | 1 | methyl | methyl | methyl | —CE$_2$—O—Ph |
| 12 | —O— | — | | methyl | methyl | methyl | —CE$_2$—O—AR |
| 13 | —NE— | —O— | 1 | methyl | methyl | hydrogen | —CE$_2$—O—AR |
| 14 | —O— | —O— | 1 | methyl | methyl | trifluoromethyl | —CE$_2$—O—AR |
| 15 | —O— | —O— | 1 | methyl | methyl | trifluoromethyl | —CE$_2$—O—AR |
| 16 | —O— | —O— | 1 | methyl | methyl | methyl | AR |

AR = 4-chlorophenyl
Ph = phenyl

TABLE 2

Elemental Analysis

| COMPOUND NO. | FOUND | | | | | THEORETICAL | | | | |
|---|---|---|---|---|---|---|---|---|---|---|
| | % C | % H | % N | % S | % Cl | % C | % H | % N | % S | % Cl |
| 1 | 50.40 | 5.87 | 18.00 | 10.26 | — | 50.31 | 5.85 | 18.05 | 10.33 | — |
| 2 | 54.39 | 6.20 | 13.59 | 10.34 | — | 54.35 | 6.19 | 13.58 | 10.36 | — |
| 3 | 53.29 | 4.50 | 15.53 | 8.89 | — | 53.32 | 4.47 | 15.55 | 8.90 | — |
| 4 | 56.79 | 4.78 | 11.69 | 8.95 | — | 56.81 | 4.77 | 11.69 | 8.92 | — |
| 5 | 69.49 | 5.35 | 11.78 | 8.99 | — | 60.49 | 5.36 | 11.76 | 8.97 | — |
| 6 | 56.98 | 5.04 | 15.64 | 8.97 | — | 56.97 | 5.06 | 15.63 | 8.95 | — |
| 7 | 51.53 | 3.45 | 12.04 | 9.19 | 10.16 | 51.51 | 3.46 | 12.01 | 9.17 | 10.14 |
| 8 | 60.69 | 5.68 | 15.74 | — | — | 60.67 | 5.66 | 15.72 | — | — |
| 9 | 63.34 | 5.63 | 12.29 | — | — | 63.33 | 5.61 | 12.31 | — | — |
| 10 | 58.41 | 4.55 | 12.80 | 9.75 | — | 58.35 | 4.59 | 12.76 | 9.73 | — |
| 11 | 56.77 | 4.78 | 11.65 | 8.92 | — | 56.81 | 4.77 | 11.69 | 8.92 | — |
| 12 | 51.87 | 4.11 | 10.65 | 8.18 | 9.08 | 51.84 | 4.09 | 10.67 | 8.14 | 9.00 |
| 13 | 50.65 | 3.75 | 11.04 | 8.41 | 9.35 | 50.60 | 3.72 | 11.06 | 8.44 | 9.33 |
| 14 | 45.52 | 2.95 | 9.38 | 7.20 | 7.91 | 45.60 | 2.93 | 9.38 | 7.16 | 7.92 |
| 15 | 45.61 | 2.92 | 9.40 | 7.17 | 7.90 | 45.60 | 2.93 | 9.38 | 7.16 | 7.92 |
| 16 | 57.39 | 4.53 | 7.41 | 8.53 | 9.44 | 57.37 | 4.55 | 7.43 | 8.51 | 9.47 |

We claim:
1. A heterobicyclic compound of general formula (I):

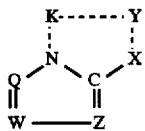

in which:
Y represents the following group:

wherein R represents a Ch group or a T group;
W represents the following group:

wherein R represents an Ra group;
Q and Z represent the following group: —N=
K represents the following group:

wherein R represents a Ch group or a T group:
X represents a sulphur atom;
T represents one of the following groups of general formula (II), (III), (IV) and (V):

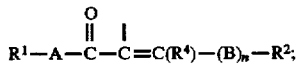  (II)

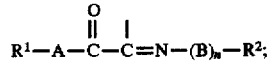  (III)

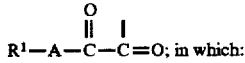  (IV)

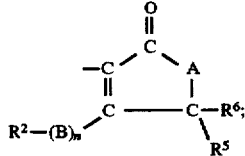  (V)

A and B, identical or different, represent an oxygen or sulphur atom or an —N(R³)— group;
R¹, R², R³, R⁴, R⁵ and R⁶, identical or different, represent a hydrogen atom or a $C_1$–$C_4$ linear or branched alkyl or haloalkyl group;
n can be 0 or 1;
Ra represents a hydrogen atom, a halogen atom selected from the group consisting of fluorine, chlorine, bromine and iodine; a cyano group; a $C_1$–$C_4$ linear or branched alkyl or haloalkyl group; a $C_1$–$C_4$ linear or branched alkoxy or haloalkoxy group; a $C_1$–$C_4$ linear or branched alkoxyalkyl or haloalkoxyalkyl group; a $C_1$–$C_4$ linear or branched carboalkoxy group; a $C_3$–$C_8$ cycloalkyl or cycloalkoxyalkyl group;
Ch represents a group of general formula (VI):

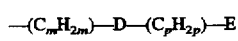  (VI)

in which:
D represents a direct bond; an oxygen, sulphur or nitrogen atom; a nitrogen atom substituted with a $C_1$–$C_3$ alkyl group; or a carbonyl group;
E represents a $C_6$,$C_{10}$ aryl group optionally substituted; a penta- or hexa-atomic heteroaryl group optionally benzocondensed and/or substituted;
m and p, identical or different, are a whole number between 0 and 4;

with the proviso that at least one of said K and Y groups contain a T group.

2. Antifungals as claimed in claim 1, wherein the T groups are: 1-methoxycarbonyl-2-methoxyethen-1-yl, 1-ethoxycarbonyl-2-methoxyethen-1-yl, 1-methoxycarbonyl-2-ethoxyethen-1-yl, 1-methoxycarbonyl-2-(1,1,2,2-tetrafluoro-ethoxy)ethen-1-yl, 1-methoxycarbonyl-2-thiomethoxyethen-1-yl, 1-methoxycarbonyl-2-ethylethen-1-yl, methoxycarbonyl-oxomethyl, methoxyiminomethoxy-carbonylmethyl, ethoxyiminomethoxycarbonyl-methyl, ethyliminomethoxycarbonylmethyl, 1-(N-methylcarbamoyl)-2-methoxyethen-1-yl, 1(N-methylcarbamoyl)-2-thiomethoxyethen-1-yl, 4-methoxy-2(5H)furanon-3-yl, 3-methyl-4-methoxy-2(5H)-furanon-3-yl, 3,3-dimethyl-4-methoxy-2(5H)-furanon-3-yl, 4-methoxy-2(5H)-pyrrolidinon-3-yl.

3. Antifungals as claimed in claim 1, wherein the Ra groups are: methyl, ethyl, trifluoromethyl, trifluoroethyl, methoxy, ethoxy, 1,1,1-trifluoroethoxy.

4. Antifungals as claimed in claim 1, wherein the penta- or hexa-atomic heterocyclic groups are the following heteroaromatic rings: pyridyl, pyrimidyl, piridazyl, thienyl, furyl, pyrrolidyl, triazolyl, imidazolyl, isooxazolyl, oxazolyl, thiazolyl.

5. Antifungals as claimed in claim 1, wherein the optionally substituted aryl or heteroaryl groups are substituted with:
one or more groups, identical or different, chosen from the following: $C_1$–$C_6$ linear or branched alkyl or haloalkyl; $C_1$–$C_6$ linear or branched alkoxy or haloalkoxy; $C_2$–$C_8$ linear or branched alkoxyalkyl; $C_1$–$C_6$ linear or branched haloalkoxyalkyl; $C_2$–$C_8$ carboalkoxy; $C_2$–$C_8$ carbamoyl; a cyano group; or a halogen atom such as fluorine, chlorine, bromine or iodine.

6. An antifungal as claimed in claim 1, consisting of 2-methyl-5-(1-methoxycarbonyl-2-methoxyethen-1-yl)-6-phenylthiazolo[3,2-b]-[1,2,4]-triazole.

7. An antifungal as claimed in claim 1, consisting of 2-methyl-5-phenoxymethyl-6-(1-methoxycarbonyl-2-methoxyethen-1-yl)-thiazolo[3,2-b]-[1,2,4]-triazole.

8. An antifungal as claimed in claim 1, consisting of 2-methyl-5-(4-chlorophenoxy)methyl-6-(1-methoxycarbonyl-2-methoxyethen-1-yl)-thiazolo[3,2-b]-[1,2,4]-triazole.

9. An antifungal as claimed in claim 1, consisting of 5-(4-chlorophenoxy)methyl-6-(1-methoxycarbonyl-2-methoxyethen-1-yl)-thiazolo[3,2-b]-[1,2,4]-triazole.

10. An antifungal as claimed in claim 1, consisting of 2-trifluoromethyl-5-(4-chlorophenoxy)methyl-6-(1-methoxycarbonyl-2-methoxyethen-1-yl)-thiazolo[3,2-b]-[1,2,4]-triazole.

11. An antifungal as claimed in claim 1, consisting of 6-(4-chlorophenyl)-5-(1-methoxycarbonyl-2-methoxyethen-1-yl)-thiazolo[2,3-c]-1,2,4-triazole.

12. A fungicidal composition containing one or more compounds as claimed in claim 1, either alone or in combination with one or more of the following: solid supports, liquid diluents, surfactants, and other active substances.

13. A method for combating fungal infections, consisting of applying a fungicidal composition claimed in claim 12 to plants, leaves, stalks, branches and roots, or onto the seeds themselves before sowing, or onto the ground in which the plant is growing.

* * * * *